United States Patent
Mueller et al.

(10) Patent No.: US 10,639,433 B2
(45) Date of Patent: May 5, 2020

(54) DEVICE FOR GAS HEATING AND HUMIDIFICATION BY MEANS OF MAGNETIC INDUCTION FOR LAPAROSCOPY

(71) Applicant: W.O.M. World of Medicine GmbH, Berlin (DE)

(72) Inventors: Bernd Mueller, Berlin (DE); Yves Koeth, Berlin (DE)

(73) Assignee: W.O.M. WORLD OF MEDICINE AG, Berlin (DE)

( * ) Notice: Subject to any disclaimer, the term of this patent is extended or adjusted under 35 U.S.C. 154(b) by 788 days.

(21) Appl. No.: 14/761,282

(22) PCT Filed: Jan. 15, 2014

(86) PCT No.: PCT/DE2014/000019
§ 371 (c)(1),
(2) Date: Jul. 15, 2015

(87) PCT Pub. No.: WO2014/111085
PCT Pub. Date: Jul. 24, 2014

(65) Prior Publication Data
US 2015/0352300 A1    Dec. 10, 2015

(30) Foreign Application Priority Data
Jan. 15, 2013    (DE) .......... 10 2013 000 491

(51) Int. Cl.
*A61M 13/00*    (2006.01)
*A61M 16/16*    (2006.01)
*A61M 16/10*    (2006.01)

(52) U.S. Cl.
CPC ......... *A61M 13/003* (2013.01); *A61M 16/108* (2014.02); *A61M 16/1095* (2014.02); *A61M 16/16* (2013.01); *A61M 2202/0225* (2013.01); *A61M 2205/3368* (2013.01); *A61M 2205/36* (2013.01); *A61M 2205/3653* (2013.01); *A61M 2205/7536* (2013.01)

(58) Field of Classification Search
CPC ............. A61M 13/003; A61M 16/108; A61M 16/1095; A61M 16/16
USPC .......................................................... 604/24
See application file for complete search history.

(56) References Cited

U.S. PATENT DOCUMENTS

| | | | |
|---|---|---|---|
| 5,411,474 A * | 5/1995 | Ott | A61M 13/003 600/560 |
| 5,810,776 A * | 9/1998 | Bacich | A61B 17/3417 604/131 |
| 6,068,609 A | 5/2000 | Ott et al. | |
| 7,975,687 B2 | 7/2011 | Grundler et al. | |
| 2004/0102731 A1 | 5/2004 | Blackhurst et al. | |
| 2006/0012057 A1 | 1/2006 | Anthony | |

(Continued)

FOREIGN PATENT DOCUMENTS

| | | |
|---|---|---|
| AU | 2008202098 A1 | 2/2009 |
| DE | 102005007773 | 9/2005 |
| EP | 1558877 | 10/2003 |

(Continued)

*Primary Examiner* — Phillip A Gray
(74) *Attorney, Agent, or Firm* — Mayer & Williams, PC; Stuart H. Mayer

(57) ABSTRACT

The present invention relates to a device for heating and humidifying gas for laparoscopy by means of magnetic induction.

21 Claims, 1 Drawing Sheet

(56) References Cited

U.S. PATENT DOCUMENTS

2006/0113690 A1    6/2006  Huddart et al.
2010/0262152 A1*  10/2010  Shadduck .......... A61B 17/8822
                                                            606/94

FOREIGN PATENT DOCUMENTS

| EP | 1386629 A1 | 2/2004 |
| EP | 0827417 | 3/2004 |
| EP | 1507568 | 3/2007 |
| EP | 2075026 A1 | 7/2009 |
| WO | 2012/135912 A1 | 10/2012 |

* cited by examiner

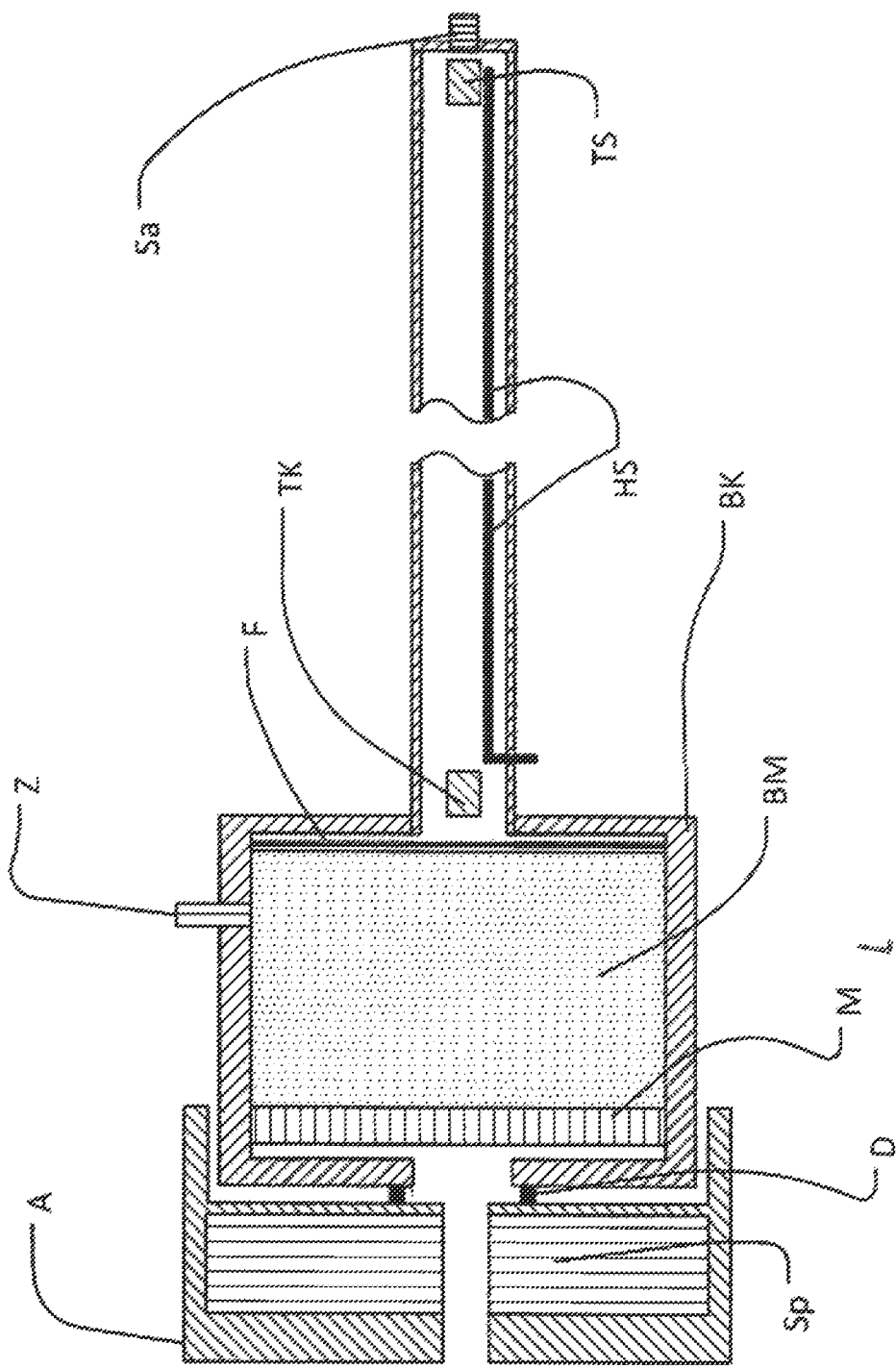

DEVICE FOR GAS HEATING AND HUMIDIFICATION BY MEANS OF MAGNETIC INDUCTION FOR LAPAROSCOPY

The present invention relates to a device for heating and humidifying gas for laparoscopy by means of magnetic induction. The present patent application claims priority of German application DE 102013000491.8 (date of filing: 15 Jan. 2013).

PRIOR ART

Laparoscopy is a medical surgery by means of which the abdominal cavity and the organs therein can visually be examined. For this purpose, small skin incisions (0.3-2 cm) in the abdominal wall are typically made, and a trocar is introduced therethrough, which in turn can accommodate an optical device. With the aid of a special endoscope (laparoscope), the abdomen can be examined. In diagnostic laparoscopy, the abdomen is just visually inspected, and in a therapeutic process, operative surgeries can also be performed.

Typically, at the beginning of the laparoscopy, the abdomen is filled with gas, in order to create a pneumoperitoneum. For this purpose, various gases have already been used, such as air, nitrogen or carbon dioxide ($CO_2$). The use of carbon dioxide gas has proven particularly successful. It was found that it is reasonable, in particular with longer laparoscopic surgeries, on the one hand to heat the introduced gas and on the other hand to humidify it. Heating the gas serves to prevent the patient from being cooled down, and to avoid a diffuse feeling of pain by the patient, which is a likely consequence of a local cooling upon the entry of cold gas. The humidification serves to prevent drying out of the inner abdominal surfaces, in order to avoid the cooling occurring thereby. For the purpose of the invention, relative gas humidities of more than 90% should be achieved. When employing this in laparoscopy, a peculiarity results in that the volume flows will strongly vary. An average gas flow of 1-3 l/min. can be assumed. If there should be, however, a larger leakage, for instance by activation of a ventilation, then immediately gas flow rates >10 l/min. are required, and these, too, should achieve the required humidity level of more than 90%.

For this purpose, prior art gives some suggestions. U.S. Pat. No. 6,068,609 describes a device that makes heating and humidifying gas for laparoscopy possible. Therein, a separate chamber is described that is equipped with a heating resistor. In the chamber is further arranged an absorbing material, such as a sponge that can be moistened. By the electric heating of the chamber, water from the humidifying means is vaporized. The described device has the disadvantage that an electrical connection is required for operating the heating resistor. This necessitates on the one hand, certain efforts in the manufacture, for instance for laying the cables, and on the other hand corresponding costs for the production of the chamber. Since the chamber is disposable, low efforts, and in particular low costs, are very important in practice.

Furthermore, it is an aim of the invention to locate the chamber not at the patient-side end, but at the device-side end. Thereby, handling of the insufflation tube is improved. Due to the size and the weight of the chamber, it may be disturbing in the near operational field to the doctor in charge.

The document DE 10 2005007773 A1 describes a device for humidifying breathing gas, wherein in a particular embodiment a water reservoir is heated by induction. Further prior art is represented by the documents EP 1507568 B1, EP 1558877 B1, and EP 0827417 B1.

It is therefore an object of the present invention to provide a simpler device for gas heating and humidifying that avoids the above disadvantages.

SOLUTION OF THE TECHNICAL PROBLEM

This technical problem is solved by the subject matter of patent claim 1. Advantageous configurations are subject matters of the sub-claims.

The essence of the present invention is the configuration of a heating element for gas heating and humidifying that permits magnetic induction. Inductive heating (or also induction heating by means of eddy currents) is a known method that needs not be explained in more detail here. For this purpose, a coil, through which a low- or medium-frequency alternating current (example: frequency: ~50-200 kHz, voltage: 10-50 volts, current: 1-5 amps) flows and which has a surface area of e.g. 750-3,000 $mm^2$, is brought in proximity of a body having an electrically conductive material, whereby an eddy current is induced in this body effecting the heating of the mentioned body. The heat generated thereby is generated immediately in the body, i.e. is not transferred by heat conduction. Inductive heating can be effected through non-conducting materials, such as for instance a plastic material, in which the heating body is arranged. The efficiency depends on the selected material, the better conductive the material is, the worse is in general the heating effect. For the purpose of the present invention, in particular heating bodies made of iron are used, for instance a cuboid of the size 30×45×2.5 mm (i.e. a face showing toward the coil having an area of 1,350 $mm^2$) with a distance to the coil of approx. 3 mm. The heating body is completely heated up, so that for heating the gas all faces of the body are available, thus, in the present example, approx. 3,075 $mm^2$. Reasonably, the thickness of the heating element will be 2-5 mm. A particular advantage of the present invention is that the heating element may accept nearly any geometric shapes and can thus easily be adapted to the available space. It is understood that the coil must have a corresponding shape and corresponding dimensions. Another advantage of the invention is that no electrical cables need to be accommodated in the tube. Further, a plurality of heating elements can be used.

According to the invention, the heating element is preferably paired with a humidifying means, such as a porous material, which has an as high as possible water absorption capacity and can be humidified by addition of water. The humidifying material should be arranged in proximity of the heating element. It may have for instance contact over the full surface with the heating element. In an alternative embodiment, there is a distance between the opposing surfaces of the heating element and of the humidifying material. With the conventional dimensions of laparoscopic instruments, in particular of the tubes and their connection elements, the distance will usually not exceed 5 cm. Preferably, the distance between the humidifying material and the surfaces of the heating element is from 0 to 1 cm, particularly preferred 1 to 5 mm. The porous material may in the simplest case be a fabric of cotton (e.g. a gauze bandage) that is capable of absorbing a certain amount of water. Alternatively and/or additionally, the following materials can be used: sponges, superabsorbing polymers (SAP), blotting paper, material made of phenol resins.

It is important that the gas flow is possibly guided such that an intense contact of the gas with the heating element and if applicable with the humidifying material is made possible. For example, the gas may be conducted through smaller holes in an iron plate. On the other side of the iron plate, the humidifying material can then be arranged, which is directly passed by the gas. Alternatively, the gas may also be conducted along the heating plate and then come into contact with the humidifying material. The distances of humidifying material and iron plate influence of course the humidifying efficiency. Insofar, they should be positioned, as described above, as close to each other as possible, e.g. 0 to 5 cm, preferably 0 to 1 cm, particularly preferred 1 to 5 mm. The heating element may have contact over the full surface with the humidifying material, in many cases, however, a small distance is desirable.

The water absorption capacity of the porous material depends of course on the respective material. For a normal surgery, approx. 200 liters gas are consumed. In order to humidify the gas to nearly 100% relative humidity, ~10 ml liquid are required. It is advantageous, when the amount of the humidifying material used can absorb this amount of liquid.

Depending on the intended duration of the laparoscopic surgery and the gas flow, it may be sufficient to humidify the porous material once before the laparoscopy. Before beginning the laparoscopic surgery, the humidifying means is humidified with water. In particular in case of longer surgeries, another humidification may be necessary. For this purpose, the device may be provided with an optional feed line that allows another addition of water. For one skilled in the art it is obvious that before the beginning of the surgery as well as if applicable during the surgery, the added water will have to be sterile.

Based on the immediate proximity between the inductively heated heating element and the humidifying means, a constant humidification of the gas in the gas flow is achieved.

Of course, a device according to the invention may include, behind the heating element, a temperature sensor that monitors the temperature of the gas supplied to the patient.

Since the gas, on its way through the insufflation tube after humidification, will cool down again to ambient temperature, the insufflation tube may be heated, too. Thereby, the already heated and humidified gas can be transported to the patient. This tube heating means may, for instance, be a heating resistor that may also include a temperature probe.

By means of the invention, the device for humidifying may be positioned at the device-side end of the insufflation tube. Thus, the device is not disturbing in the near operational field to the doctor in charge.

By using the induction technology, the production costs of the disposable tube can significantly be reduced. On the one hand, components such as for instance electrical contacts are not required, on the other hand the production time and thus the cost is reduced.

The present invention will be further illustrated by the following example, which however is not intended to be limiting.

EXAMPLE

A heating element made of iron, shaped as a plate of the size 45×30×3 mm is positioned in a chamber with the inner dimensions 30×45×18 mm, consisting of a biocompatible plastic material. The heating element is provided with a plurality of holes, through which the gas flows during insufflation. The remaining space of the chamber is filled with a gauze bandage (material: cotton). Finally, a hydrophobic filter with the dimensions 45×30 mm is mounted in place.

The thus formed chamber is connected, at one side, to a gas reservoir, and is provided, at the other side, with a tube that ends in a Veress needle.

An access to the chamber allows the humidification of the humidifying material with sterile water.

At the outlet of the chamber, a temperature probe is arranged in the tube disposed therebehind. Thereby, the temperature of the gas leaving the chamber can be controlled. In the further course of the tube is positioned a heating wire that keeps the gas temperature within the tube constant.

The coil needed for the induction including the necessary electronic system is accommodated in the insufflator and is not part of the tube set. The described chamber is clamped into position in a unit at the device, which includes the induction section (this is illustrated in more detail in FIG. 1).

Before the surgery, the humidifying means is wetted with 10 ml water. Through the described device, up to 50 l $CO_2$ per minute can be conducted. The heating power is adjusted, via the magnetic alternating field, to the respective demand, i.e. when the temperature at the gas outlet of the chamber drops, a higher heating power is adjusted, when the temperature rises, the heating power is reduced. The gas temperature in the insufflation tube arranged behind the chamber is held constant at approx. 37° C. For the induction of the alternating field, a voltage of 24 volts with a frequency of approx. 120 kHz is applied. This results in a heating power of up to 60 watts. The relative gas humidity reaches values of approx. 95%.

LIST OF REFERENCES FOR FIG. 1

A receptacle at the device for insufflation tube
Z feed line for humidification of the porous material
F filter
TK temperature measurement behind chamber
Sa tube connection patient-side end
TS temperature measurement at tube end
HS heating wire in tube
BK humidification chamber
BM humidifying means
M metal plate with holes
D seal
Sp coil

The invention claimed is:
1. A device for heating a gas flow for use in laparoscopy, the device comprising:
a heating element within a chamber;
a means for introducing a gas flow along said heating element,
wherein the gas flow is conducted over said heating element that is inductively heated,
wherein the heating element includes an electrically conductive plate disposed in proximity to a coil so that an alternating current generated by the coil induces eddy currents in the electrically conducting plate, the electrically conductive plate having a plurality of holes extending therethrough through which the gas flow is conducted during insufflation.

2. The device according to claim 1, further comprising a humidifying material, wherein the gas flow is conducted, in addition to over said heating element, over said humidifying material.

3. The device according to claim 2, wherein the humidifying material has a distance to the heating element of 0 to 5 cm.

4. The device according to claim 2 wherein the heating element and the humidifying means are components of the chamber, through which the gas flow is conducted.

5. The device according to claim 4, wherein the chamber includes an access for humidification of the humidifying material.

6. The device according to claim 4 wherein the chamber includes at a patient-side end outlet a hydrophobic filter.

7. The device according to claim 6, further comprising a temperature probe that monitors a temperature of the gas at the patient-side end outlet of said chamber.

8. The device according to claim 1, further comprising a heated tube at the chamber outlet.

9. The device according to claim 8, wherein the heated tube is heated by a heating wire.

10. The device according to claim 9, wherein a temperature probe monitors the temperature of the gas at the chamber outlet.

11. The device according to claim 1, wherein the heating element is made of iron.

12. The device according to claim 1, wherein the surface area of the heating element facing the coil is between 750 to 3,000 mm$^2$.

13. The device according to claim 1, wherein the humidifying comprises cotton fabric, sponges, super-absorbing polymers (SAP), blotting paper, or material made of phenol resins.

14. A device for heating a gas flow for use in laparoscopy comprising:
a chamber having an input end and an opposing output end, the input end connectable to an receptacle including an induction section and also a means for introducing a gas flow;
a heating element within said chamber;
wherein the gas flow is conducted over said heating element that is inductively heated,
wherein the heating element includes an electrically conductive plate disposed in proximity to a coil so that an alternating current generated by the coil induces eddy currents in the electrically conducting plate, the electrically conductive plate having a plurality of holes extending therethrough through which the gas flow is conducted during insufflation.

15. The device according to claim 14 wherein said chamber comprises biocompatible plastic material.

16. The device according to claim 14 wherein the coil is located external to the chamber.

17. The device according to claim 14 wherein the input end of said chamber is connectable to a gas reservoir, and at the opposing output end is connect to a tube.

18. The device according to claim 14 wherein said tube ends in a Veress needle.

19. The device according to claim 14, further comprising a humidifying material, wherein the gas flow is conducted over said heating element and over said humidifying material.

20. The device according to claim 14 further comprising a hydrophobic filter within said chamber.

21. A device for heating a gas flow for use in laparoscopy, comprising:
a heating element for heating the gas flow, the heating element being inductively heated and including holes through which the gas flow is conducted, wherein the heating element includes an electrically conductive plate disposed in proximity to a coil so that an alternating current generated by the coil induces eddy currents in the electrically conducting plate;
a humidifying material over which the gas flow is conducted, the humidifying material being separated from the heating element by distance of between 0 and 5 cm, the humidifying material and the heating element being components of a separate chamber through which the gas flow is conducted; and
wherein the device is positioned at a device-side end of an insufflation hose.

* * * * *